United States Patent [19]

Kamalov et al.

[11] Patent Number: 5,148,031
[45] Date of Patent: Sep. 15, 1992

[54] DEVICE FOR OBTAINING SPATIAL AND TIME CHARACTERISTICS OF A WEAK OPTICAL RADIATION FROM AN OBJECT

[76] Inventors: Valei F. Kamalov, ulitsa Ramenka, 9, korpus 1, kv. 17; Bulat N. Toleutaev, Leninskie gory, MGU, korpus D, komnata 332; Alexandr P. Shkurinov, Lomonosovsky prospekt, 23, kv. 413, all of Moscow; Mikhail R. Ainbund, ulitsa Manchesterskaya, 6, kv. 10; Georgy A. Menshikov, prospekt Bolshevikov, 3, korpus 1, kv. 15, both of Leningrad, all of U.S.S.R.

[21] Appl. No.: 717,076

[22] Filed: Jun. 18, 1991

[51] Int. Cl.[5] ............................................. G01N 21/64
[52] U.S. Cl. ................................. 250/458.1; 356/317; 356/318
[58] Field of Search ............................. 356/318, 317; 250/458.1

[56] References Cited

U.S. PATENT DOCUMENTS 3,965,354  6/1976  Fletcher et al. ................... 250/336.1
4,662,748  5/1987  Tanaka et al. ...................... 356/317

OTHER PUBLICATIONS

Review of Scientific Instruments, 1987, v. 58, No. 12, M. Lampton et al., "Delay line anodes for microchannel-plate spectrometers", pp. 2298-2305.
Review of Scientific Instruments, 1987, v. 58, No. 9, W. G. McMullen et al. "Simultaneous subnancsecond timing information and 2D spatial information from imaging photomultiplier tubes", pp. 1626-1628.

Primary Examiner—Constantine Hannaher
Attorney, Agent, or Firm—Beveridge, DeGrandi & Weilacher

[57] ABSTRACT

A device for obtaining spatial and time characteristics of a weak optical radiation from an object comprises an optical pulsed radiator for irradiating the test object, a photoelectronic multiplier with an anode formed by a delay line, for detecting the radiation from the object, and two time-to-amplitude converters with their start-inputs connected to the output of a generator of electric pulses synchronous with the pulses of the optical radiator, and with their stop-inputs connected to the ends of the delay line. The outputs of the converters are connected to the inputs of the adder circuit and the subtractor circuit whose outputs are connected to a data storage and processing unit.

1 Claim, 1 Drawing Sheet

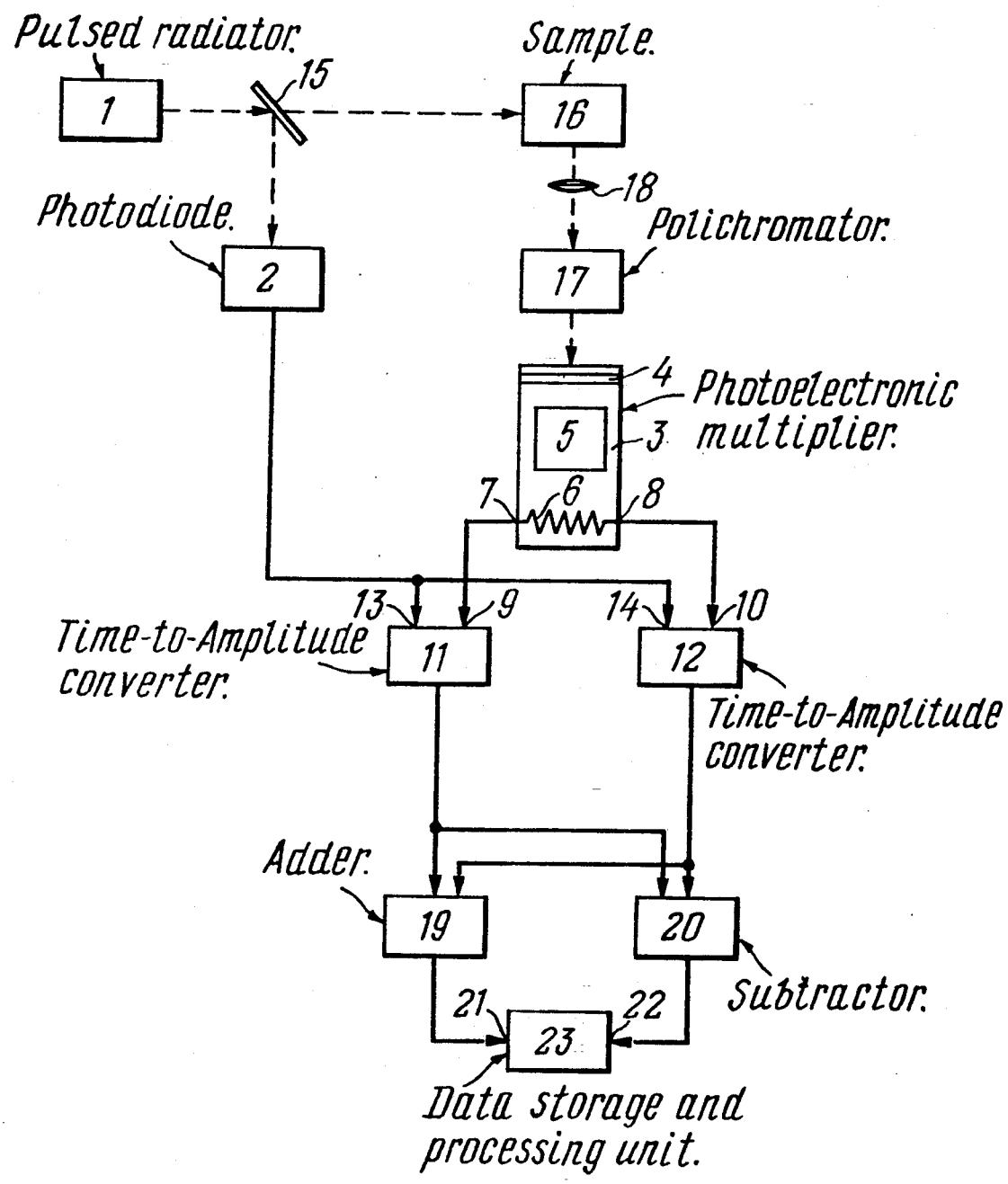

DEVICE FOR OBTAINING SPATIAL AND TIME CHARACTERISTICS OF A WEAK OPTICAL RADIATION FROM AN OBJECT

FIELD OF THE INVENTION

The invention relates to the area of optical and electronic instrument engineering and particularly, to devices used to obtain weak optical radiation characteristics, the radiation time lying within the picosecond and nanosecond regions. The invention can be used in optical spectroscopy, namely, in medical, microbiological, microelectronic, geological etc. investigation, e.g. when studying the processes such as optical excitation energy relaxation in atoms, molecules and crystals. The invention provides information on the lifetimes of the excited electron states of the molecules in solutions, on the carrier relaxation rates in crystals, on the photochemical transformation channels, etc. In addition, when using sufficiently powerful radiation sources and associated optical devices, the invention may serve as the basis for building a system aimed at investigating remote objects, such as finding the size and position of spaceships, or sounding of raised macroobjects.

BACKGROUND OF THE INVENTION

Known in the art is a device for determining time characteristics of a weak optical radiation ("Kvantovaya Elektronika, Moscow, 1987, v. 14, No. 6, V. F. Kamalov et al. "Lazerny subnanosekundy fluorestsentny spektrometr so schetom odinochnykh fotonov", p. 1303–1308) comprising a pulsed laser radiator with a holder for the test object, a photoelectronic multiplier, a photodiode, and a time-to-amplitude converter with its output connected to a multichannel analyzer, all arranged in the path of the laser beam. A variable-wavelength monochromator is placed before the photocathode of the photoelectronic multiplier. The start-input of the time-amplitude converter is connected to the photodiode output, and its stop-input, through a discriminator, to the anode of the photoelectronic multiplier. The laser beam is applied to the photodiode and to the test object, causing its fluorescence. The radiation from an object, of a specific wavelength to which the monochromator is turned, is converted to electric signals by the photoelectronic multiplier. The time-to-amplitude converter develops a voltage in proportion to the time period by which the instant of light quantum emission from an object is delayed relative to the instant of its irradiation (as determined by the photodiode pulse). The multichannel analyzer stores the measurement results in the channel corresponding to the time delay measured. When a sufficient number of time-to-amplitude converter outputs has been stored, the multichannel analyzer produces an amplitude-time characteristic of the radiation being investigated at a single fixed wavelength.

Known in the art is a device for obtaining spatial characteristics of weak luminescence sources (Review of Scientific Instruments, 1987, v. 58, No. 12, M. Lampton et al. "Delay line anodes for microchannel-plate-spectrometers", p. 2298–2305) comprising a photodetector with microchannel plates plates and a delay line anode system with the start-and stop-inputs of the time interval meter connected thereto through discriminators. The radiation from the test object initiates a localized charge derived from a specific point of the detector photocathode, which is applied to a point in the delay line whose coordinate corresponds to that of the charge generation point on the photocathode and consequently, to the coordinate of the luminescent point on the object. The localized charge produced in the delay line is the source of two electric pulses travelling towards its ends. The time-interval meter is started by one of these pulses and stopped by the other of them. The measured interval between the arrival times of the electric pulses coming to the ends of the delay line is a measure of the space position on the photocathode to which the photon from the test object has come. By means of storing the measurement results, it is possible to obtain information about the spatial distribution of light intensity.

So each of the above mentioned devices enables only one characteristic of the weak optical radiation to be obtained, namely: either the spatial characteristic or the time characteristic. However, in order to investigate objects whole luminescence changes its space positions with time, or is a result of superposition of several components spaced apart in time, a simultaneous measurement of both spatial and time characteristics of the radiation is necessary. So, for example, an important task of optical spectroscopy is separation of Raman scattering, fluorescence and phosphorescence spectra emitted by the molecules with different delays after pulse excitation. Besides, the glow spectra may change with time due to restructuring or energy relaxation processes. It is impossible to solve this problem by alternately measuring, first, spatial and then, time characteristics.

Also known is a device for determining weak optical radiation characteristics for an object (Review of Scientific Instruments, 1987, v. 58, No. 9, W. G. McMullan et al. "Simultaneous subnanosecond timing information and 2D spatial information from imaging photomultiplier tubes", p. 1626–1628) providing simultaneous timing and spatial information about the radiation investigated. The device comprises a photoelectronic multiplier with microchannel plates, and a two-dimensional resistive anode which is essentially a delay line. The anode has two pairs of terminals disposed on its ends at right angles to each other. The anode terminals are connected to a locating computer coupled with the personal computer.

Further, the device comprises a pulsed laser radiator for irradiating an object mounted in a holder, an avalanche photodiode to which part of the pulsed laser radiation is diverted, and a time-to-amplitude converter connected, through an amplitude pulse analyzer, to a second personal computer. The signal applied to the start-input of the time-to-amplitude converter is derived from an RC-circuit connected to the output electrode of one of the microchannel plates of the photoelectronic multiplier, while the stop-input of the time-to-amplitude converter is connected, through an amplifier and a discriminator, to the output of the avalanche photodiode generating electric pulses in synchronism with the laser radiator pulses. Since the microchannel plate pulse has a positive polarity and a very low amplitude, amplifiers, an inverter, and a discriminator are inserted between the RC-circuit and the stop-input of the time-to-amplitude converter.

The locating computer determines the two-dimensional space coordinate of the glow source or, with a spectroscopic mode of operation of the device, when the radiation to be investigated is linearly dispersed over the wavelength at the photocathode of the photoelectronic multiplier, the measurement results along one of the axes used to obtain information on the wavelength. The personal computer provides the storage and processing of the measurement result and produces the spectrum of the luminescence investigated or the space positions of the luminescence source.

The time-to-amplitude converter generates a voltage proportional to the time interval between the instant the object is irradiated and the instant the electric signal makes its appearance in the photoelectronic multiplier, which corresponds to the moment at which the object radiates a light quantum. The time-to-amplitude converter output voltage is converted to digital form by an amplitude pulse analyzer, and the conversion results are entered into the second personal computer and displayed as an amplitude-time characteristic.

One disadvantage of the device resides in its complexity due to the presence of two independent measuring channels, the first of them using signals derived from the photoelectronic multiplier anode serving to obtain the spatial characteristics of the radiation, the other one using signals from the microchannel plate electrode being designed to obtain the timing characteristics. Since these channels are not synchronized, noise pulses are apt to be detected in the space position measuring channel (i.e. coming from the anode of the photoelectronic multiplier). These noise pulses may be mistaken for a desired signal and so cause a false indication to appear.

Besides, the device fails to provide a sufficient accuracy of obtaining the time characteristics of the radiation, since a pulse from the electrode of the microchannel plate of the photoelectronic multiplier is used as the timing signal in the "time" measuring channel. This pulse has a small amplitude and is required to be subsequently amplified, so that ultimately, the timing information-bearing signal may be hard to detect against the noise background. Further, the terminal of the microchannel plate, from which the timing signal is derived, is at a potential relative to the case of the device (i.e. the anode of the photoelectronic multiplier), thus complicating the maintenance of the device.

SUMMARY OF THE INVENTION

It is an object of the invention to simplify the device for obtaining spatial and time characteristics of a weak optical radiation from an object.

It is another object of the invention to increase the accuracy of evaluating spatial and time characteristics of a weak optical radiation from an object.

A further object of the invention is to provide a device for obtaining spatial and time characteristics of a weak optical radiation from an object, such that a common measuring channel is used to obtain the spatial and timing information on the radiation investigated, with the signals derived from the anode of the photomultiplier implemented in the form of a delay line serving as message signals.

With these objects in view, the device for determining characteristics, of a weak optical radiation from an object comprises a holder for the test object, an optical pulse radiator for irradiating the test object to produce a weak optical radiation from the object, a photoelectronic multiplier with an anode implemented in the form of a delay line for conversion of said weak optical radiation into electric signals, a means for generating electric pulses in synchronism with the optical radiation pulses, two time-to-amplitude converters, an adder circuit, a substractor circuit, and a data storage and processing unit. The first inputs of the time-to-amplitude converters are connected to the output of the electric pulse generator, and the second input of the first time-to-amplitude converter is connected to one of the ends of the delay line, its other end being connected to the second input of the second time-to-amplitude converter. The outputs of the time-to-amplitude converters are connected to the inputs of the adder and to the inputs of the subtractor, with their outputs connected to the inputs of the data storage and processing unit.

Introduction into the device of a second time-to-amplitude converter, as well as an adder and a subtractor, connected to the outputs of both the time-to-amplitude converters, provides a common measuring channel to be set up in the device for obtaining both the spatial and timing information about the optical radiation investigated. In this measuring channel, the information-bearing signals applied to the time-to-amplitude converters are the signals derived from the terminal ends of the delay line, i.e. of the anode of the photoelectronic multiplier. In this case, as will be shown hereinbelow in the detailed description of the invention, the adder output is a signal proportional to time delay of the instant the photon is emitted by the test object with respect to the driving pulse of the optical radiator, while the subtractor output is a signal proportional to the space position of the source of luminescence. The common measuring channel present in the device leads to its simplified circuit. The accuracy of obtaining time characteristics of the radiation in the device is improved, according to the invention, in the first place, owing to the fact that the signal from the anode of the photoelectronic multiplier (unlike the signal from the electrode of the microchannel plate) has an amplitude sufficient to make a reliable detection. Secondly, synchronization of the two time-to-amplitude converters by a single generator results in noise reduction, since the time-to-amplitude converter detects the signal in a narrow time interval. Synchronization of the time-to-amplitude converters also enables the measurement results for both the spatial and the time coordinate to be locked to one event, namely, detection of an emitted photon.

These and other objects and advantages of the present invention will be more apparent from the following detailed description of its preferred embodiment, with the accompanying drawing.

BRIEF DESCRIPTION OF THE DRAWING

The drawing represents a block schematic diagram of a device for obtaining spatial and time characteristics of a weak optical radiation from an object, according to the invention.

DESCRIPTION OF THE PREFERRED EMBODIMENT OF THE INVENTION

A device for obtaining spatial and time characteristics of a weak optical radiation from an object comprises an optical pulsed radiator such as a laser pulsed radiator 1, a photodiode 2 and a photoelectronic multiplier 3 for detecting the radiation to be investigated, including a photocathode 4, a multiplying system 5 formed, e.g., by the microchannel plates, and an anode formed by a delay line 6. Terminal ends 7 and 8 of the delay line 6 are connected to stop-inputs 9 and 10 of time-to-amplitude converters 11 and 12, respectively. Start-inputs 13 and 14 of the time-to-amplitude converters 11 and 12, respectively, are connected to the output of the photodiode 2. Placed in the beam propagation path of the laser radiator 1 is a semi-transparent mirror 15 or some other means for splitting the beam into two sub-beams, one of them being directed to the photodiode 2 and the other to the test object mounted in holder 16 (in the form of a cell, if the test object is a solution or in the form of a clamp, if it is a solid body), so that the radiation excited by the laser beam in the object comes to the photocathode 4 to the photoelectronic multiplier 3. To obtain the spectral characteristics of the object luminescence, a polychromator 17 or some other dispersive element may be placed before the photocathode 4. A lens 18 serves to display an image of the object on the photocathode 4 or on the input slit of the polychromator 17, if any.

The generator of electric pulses synchronous with the pulses of the laser radiator 1 may be a photoelectronic multiplier or some other photoelectric device, rather than the photodiode 2. Also a flash gaseous-discharge lamp or a continuous-glow tube with an optical modulator may be used instead of the laser pulsed radiator 1.

According to the invention, the device also comprises an adder circuit 19 and a subtractor circuit 20, the inputs of either of them being connected to the output of the time-to-amplitude converters 11 and 12. The output of the adder 19 and the output of the subtractor 20 are connected to input 21 and 22 of a data storage and processing unit 23, respectively, which may be in the form of a personal computer.

The operation of the device now follows.

The test object is placed within the holder 16. The laser radiator 1 is switched on, producing short-duration (e.g. picosecond) light pulses. Part of the pulsed radiation of the laser is refected by the semi-transparent mirror 15 to the photodiode 2 which generates electric pulses synchronous with the laser pulses. These electric pulse are applied to the startinputs 13, 14 of the time-to-amplitude converters 11, 12, triggering them. The rest of the laser radiation passes the mirror 15 and irradiates the object, resulting in an optical pulsed radiation whose characteristics are to be determined. The photoelectronic multiplier 3 detecting this radiation operates in a single-electron mode. The photoelectron emitted by the photocathode 4 of the photoelectronic multiplier 3, on passing the multiplying system 5, produces an electric charge arriving at a particular point of the delay line 6 whose coordinate corresponds to that of the point on the photocathode 4 from which the photoelectron has been emitted, and consequently, to the coordinate of the point on the object from which the photon of the radiation being investigated has been emitted, or else, to the wavelength of the photon emitted by the object, provided the polychromator 17 is mounted in the device.

The electric charge at the delay line 6, after it has been split into two parts propagates towards its terminal ends 7 and 8, producing signals that cause the time-to-amplitude converters 11 and 12 to stop through their stop-inputs 9 and 10, respectively. Each of the time-to-amplitude converters 11 and 12 is a device with its output voltage proportional to the time interval between the signals arriving at its start-input and stop-input. Accordingly, the output voltage $U_1$ of the time-to-amplitude converter 11 is proportional to the time interval $\Delta t + X/V$, while the output voltage $U_2$ of the time-to-amplitude converter 12 is proportional to the time interval $\Delta t + (1-X)/V$, where $\Delta t$ is the time interval between the pulse of the photodiode 2 and the arrival time of the charge coming to the delay line 6, 1 is the length of the delay line 6, V is the charge propagation speed, and X is the coordinate of the point at which the charge strikes the delay line 6, which in this case is the spacing between this point and the line end 7. The output voltage of the subtractor 20, which is equal to the difference $U_1 - U_2$, is proportional to $(2X-1)/V$ i.e. it bears information about the coordinate X to which the coordinate of the glow source corresponds. The adder circuit 19 adds the voltage $U_1$ and $U_2$ together, giving an output voltage proportional to $2\Delta t + 1/V$, i.e. bearing information about the arrival time of the photon of the optical radiation investigated coming to the photoelectronic multiplier 3, relative to the laser pulse that produced it. The outputs of the adder circuit 19 and the subtractor circuit 20 are applied to the inputs 21 and 22 of the data storage and processing unit 23, respectively, where these signals are stored. With the polychromator 17 provided in the device, the spectral characteristics of the radiation is obtained instead of its space positions, since because of the dispersion of the radiation investigated, the coordinate of the point where the photon strikes the photocathode 4 will be determined by the wavelength of this photon.

Owing to the fact that the pulses of the photodiode 2 are used as triggering signals for both of the time-to-amplitude converters 12 and 13, and that the signals of the photoelectronic multiplier 3 are only detected by the time-to-amplitude converters within a narrow time range, all the noise pulses falling outside this range miss the measuring path. So if the number of the photoelectronic multiplier noise pulses is equal to $10^3$ pulses per second, and the conversion range of the time-to-amplitude converters is 100 ns, the probability of noise pulse detection is substantially less than one sample per second, even with the high repetition rate of the pulsed laser radiator ($10^4 \ldots 10^5$ Hz). This provides a high measurement accuracy.

It is obvious that in order to obtain two-dimentional space positions of the radiation investigated, the photoelectronic multiplier 3 may be provided with another delay line (not shown in the drawing) at right angles to the delay line 6. Furthermore, in this case, the device must additionally include either another pair of time-to-amplitude converters with their stop-inputs connected to the terminal ends of the second delay line and another subtractor circuit with its inputs connected to the outputs of these time-to-amplitude converters, or else it must include one time-to-amplitude converter with its inputs connected to the terminal ends of the second delay line.

What is claimed is:

1. A device for obtaining spatial and time characteristics of a weak optical radiation from an object, comprising:

a holder for the test object, an optical pulsed radiator for irradiating said object to produce a weak optical radiation from the object, a photoelectronic multiplier with an anode formed by a delay line having a first end and a second end, for conversion of said weak optical radiation to electric signals, an electric pulse generator for generating pulses synchronous with the pulses of said optical radiator, said generator including an output, a first time-to-amplitude converter having a first input connected to said output of said generator, a second input connected to said first end of said delay line, and an output, a second time-to-amplitude converter having a first input connected to said output of said generator, a second input connected to said second end of said delay line, and an output, an adder circuit having a first input connected to said output of said first time-to-amplitude converter, a second input connected to said output of the second time-to-amplitude converter, and an output, a subtractor circuit having a first input connected to said output of said first time-to-amplitude converter, a second input connected to said output of said second time-to-amplitude converter, and an output, and a data storage and processing unit having a first input connected to said output of said adder circuit, and a second input connected to said output of said subtractor circuit.

* * * * *